United States Patent
Consigny

(10) Patent No.: US 9,554,822 B2
(45) Date of Patent: Jan. 31, 2017

(54) THROMBECTOMY CATHETER WITH ASPIRATION AND GUIDEWIRE LUMENS DEFINING AN ASYMMETRICAL TAPER AND CUTTING EDGE WITH OFFSET TIP

(75) Inventor: Paul Consigny, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 13/224,653

(22) Filed: Sep. 2, 2011

(65) Prior Publication Data

US 2013/0060206 A1    Mar. 7, 2013

(51) Int. Cl.
| | | |
|---|---|---|
| *A61B 17/3207* | (2006.01) | |
| *A61M 1/00* | (2006.01) | |
| *A61M 25/00* | (2006.01) | |
| *A61B 17/22* | (2006.01) | |

(52) U.S. Cl.
CPC ... *A61B 17/3207* (2013.01); *A61B 17/320708* (2013.01); *A61M 1/008* (2013.01); *A61B 2017/22039* (2013.01); *A61B 2017/22079* (2013.01); *A61M 25/001* (2013.01); *A61M 25/0071* (2013.01); *A61M 25/0082* (2013.01)

(58) Field of Classification Search
CPC .............. A61M 25/0068; A61M 25/0071; A61M 1/008; A61B 2017/3458; A61B 2017/320084; A61B 2017/320072; A61B 17/32; A61B 2017/32008; A61B 17/3207
USPC ............ 604/524, 509, 585, 529; 600/585
See application file for complete search history.

(56) References Cited

U.S. PATENT DOCUMENTS

| | | | | | |
|---|---|---|---|---|---|
| 2,466,042 | A | * | 4/1949 | Reich ................. | A61F 7/123 138/93 |
| 4,058,121 | A | * | 11/1977 | Choksi ............... | A61J 1/2096 604/274 |
| 4,385,631 | A | * | 5/1983 | Uthmann ............ | A61M 5/1582 604/284 |
| 4,568,329 | A | * | 2/1986 | Mahurkar ........... | A61M 5/1582 604/43 |
| 4,588,398 | A | * | 5/1986 | Daugherty .......... | A61M 25/0606 604/164.01 |
| 4,601,713 | A | * | 7/1986 | Fuqua ................. | A61M 25/0023 604/103.14 |
| 4,738,666 | A | * | 4/1988 | Fuqua ................. | A61M 25/0023 604/103.05 |
| 4,762,129 | A | * | 8/1988 | Bonzel ................ | A61M 25/104 604/103.1 |
| 4,909,252 | A | * | 3/1990 | Goldberger ......... | 606/194 |
| 4,950,232 | A | * | 8/1990 | Ruzicka et al. .... | 604/43 |
| 4,976,703 | A | * | 12/1990 | Franetzki ........... | A61M 25/0045 604/247 |
| 5,071,413 | A | * | 12/1991 | Utterberg ........... | A61M 5/162 604/411 |
| 5,084,022 | A | * | 1/1992 | Claude ................ | A61M 25/09 600/585 |
| 5,106,368 | A | * | 4/1992 | Uldall ................. | A61M 25/003 604/178 |
| 5,135,489 | A | * | 8/1992 | Jepson ................ | A61J 1/2089 600/578 |

(Continued)

*Primary Examiner* — Bhisma Mehta
*Assistant Examiner* — Matthew A Engel
(74) *Attorney, Agent, or Firm* — Randy Shen; Blakely, Sokoloff, Taylor & Zafman LLP

(57) ABSTRACT

The subject matter relates a catheter having a helical or spiral tip defining an aspiration port for removing obstructions from blood vessels.

20 Claims, 4 Drawing Sheets

(56) References Cited

U.S. PATENT DOCUMENTS

| | | | | |
|---|---|---|---|---|
| 5,163,921 A | * | 11/1992 | Feiring | A61M 25/0075 604/247 |
| 5,235,977 A | * | 8/1993 | Hirschberg | A61N 1/3918 607/123 |
| 5,330,444 A | * | 7/1994 | Webler | A61M 25/0068 604/265 |
| 5,379,779 A | * | 1/1995 | Rowland | A61M 25/09 600/585 |
| 5,423,799 A | * | 6/1995 | Shiu | A61B 17/320758 606/159 |
| 5,458,568 A | | 10/1995 | Racchini | |
| 5,632,755 A | * | 5/1997 | Nordgren | A61B 17/32075 604/22 |
| 5,845,646 A | * | 12/1998 | Lemelson | A61B 17/320758 128/899 |
| 5,879,361 A | * | 3/1999 | Nash | A61B 17/22 606/159 |
| 6,001,112 A | * | 12/1999 | Taylor | A61B 17/320758 606/159 |
| 6,129,706 A | | 10/2000 | Janacek | |
| 6,286,514 B1 | * | 9/2001 | Lemelson | A61B 17/320758 128/899 |
| 6,355,026 B1 | * | 3/2002 | Mick | A61M 25/0041 604/523 |
| 6,450,988 B1 | * | 9/2002 | Bradshaw | A61N 5/1002 600/3 |
| 6,576,001 B2 | * | 6/2003 | Werneth | A61F 7/12 604/264 |
| 6,585,926 B1 | | 7/2003 | Mirzaee | |
| 6,755,851 B2 | * | 6/2004 | Noda | A61F 7/12 604/113 |
| 6,770,038 B2 | * | 8/2004 | Balbierz | A61M 25/0612 600/435 |
| 7,273,471 B1 | | 9/2007 | Wang | |
| 7,335,184 B2 | | 2/2008 | Laguna | |
| 7,566,333 B2 | * | 7/2009 | Van Wyk | A61B 18/1485 606/41 |
| 7,569,029 B2 | * | 8/2009 | Clark | A61M 25/0023 604/266 |
| 8,021,321 B2 | * | 9/2011 | Zawacki | A61M 1/3653 604/29 |
| 8,066,660 B2 | * | 11/2011 | Gregersen | A61M 1/3653 604/29 |
| 8,075,519 B2 | * | 12/2011 | Min | A61M 25/0084 604/104 |
| 8,092,415 B2 | * | 1/2012 | Moehle et al. | 604/6.16 |
| 8,323,227 B2 | * | 12/2012 | Hamatake | 604/264 |
| 2002/0091430 A1 | * | 7/2002 | Dobak, III | A61B 18/02 607/105 |
| 2004/0193102 A1 | * | 9/2004 | Haggstrom | A61M 1/3661 604/43 |
| 2006/0136032 A1 | | 6/2006 | Legarda | |
| 2006/0189929 A1 | | 8/2006 | Lary | |
| 2006/0271154 A1 | | 11/2006 | Woodall | |
| 2009/0118661 A1 | * | 5/2009 | Moehle | A61M 25/0068 604/6.16 |
| 2009/0192435 A1 | * | 7/2009 | Gregersen | A61M 1/3653 604/6.16 |
| 2013/0060206 A1 | * | 3/2013 | Consigny | A61M 1/008 604/265 |

* cited by examiner

THROMBECTOMY CATHETER WITH ASPIRATION AND GUIDEWIRE LUMENS DEFINING AN ASYMMETRICAL TAPER AND CUTTING EDGE WITH OFFSET TIP

TECHNICAL FIELD

The subject matter relates to removing emboli from blood vessels using a surgical procedure. More particularly, the subject matter relates to removing a thrombus from a blood vessel using a catheter with a spiral cutting tip.

BACKGROUND

A thrombus, or blood clot, is the final product of the blood coagulation step in hemostasis. Thrombi can form in various parts of the human vasculature, such as in blood veins and arteries. For example, if a thrombus forms in a small artery, it may completely block the flow of blood through the artery, leading to necrosis of the tissue supplied by the blood vessel. If the thrombi become dislodged, forming emboli, they can cause serious conditions such as an ischemic stroke. Therefore, many techniques have been developed for the removal of thrombi. This procedure is commonly referred to as a thrombectomy.

A thrombectomy is typically performed using a catheter. In some instances, the catheter is outfit with an inflatable balloon attached to its tip. This is commonly referred to a Fogarty catheter. The catheter tip is passed beyond the clot, the balloon is inflated, and the thrombus is removed by withdrawing the catheter. The inflatable balloon may also be used to administer pharmacologic treatment wherein thrombolytic agents (e.g., streptokinase, urokinase, tissue plasminogen activator (TPA)) and/or anticoagulant drugs (e.g., heparin, warfarin) are administered in an effort to dissolve and prevent further growth of the clot. Possible complications of balloon thrombectomy include endothelial denudation, vessel wall injury, and intimal lesions, which can lead to another thrombosis. The vessel may also be affected by a dissection or rupture or causing cholesterol embolism from atherosclerotic plaques.

Catheter thrombectomy may also be performed using aspiration, wherein the thrombus is removed by suction, or by surgical thrombectomy, wherein the thrombus is detached by surgical removal following incision into the blood vessel by open surgery. Open surgical thrombus-removing procedures can, in many cases, be used to rapidly remove clots from the lumens of blood vessels, but such open surgical procedures are notoriously invasive, often require general anesthesia, and the use of such open surgical procedures is generally limited to blood vessels which are located in surgically accessible areas of the body. For example, many patients suffer strokes due to the lodging of blood clots in small arteries located in surgically inaccessible areas of their brains and, thus, are not candidates for open surgical treatment.

Thus, there exists a need for the development of new surgical thrombectomy catheter that is advanceable and exchangeable over pre-inserted small diameter guidewires and that is capable of safely removing thrombi or other matter from blood vessels.

SUMMARY

In accordance with one aspect of the subject matter, disclosed is a catheter for removing an obstruction, such as a thrombus, from a blood vessel. In some embodiments, the catheter comprises an elongate flexible catheter body comprising a proximal end, a distal end, and at least one guidewire lumen extending therethrough. The distal end of the catheter comprises a tip having a cutting edge spirally tapered along a length of the catheter to define an oblique angle.

In some embodiments, the angle of the asymmetrical helical tip is approximately 10 degrees to 80 degrees relative to the longitudinal axis of the catheter body. The length of the tapered spiral tip may be approximately 5 mm to 20 mm. In other embodiments, the external diameter of the catheter is approximately 3 French to 8 French. For example, with a 3 French catheter, the angle of the spiral tip may be approximately 10 degrees and the length of the tapered tip may be approximately 0.2 mm or, with an 8F catheter, the angle of the spiral tip may be approximately 80 degrees and the length of the spiral tip may be approximately 50 mm.

The direction of the spiral on the catheter may be clockwise or counterclockwise. The direction of the spiral may be determined by the age of the obstruction, the direction of curvature of the artery in which the catheter is placed, or the handedness of the inverventionalist using the catheter. For example, the direction of curvature can have a 90° point angle, 118 point angle or 135 point angle. The cutting edge of the spiral catheter is preferably sinusoidal.

In other embodiments, the catheter lumen extends along the longitudinal edge of the spiral tip. The tip may have a leading edge along the longitudinal axis and a trailing edge along the longitudinal axis, the leading edge disposed distal of the trailing edge.

In some embodiments, the guidewire lumen contains a guidewire for guiding the catheter in a blood vessel. In another embodiment, the catheter may be in an RX system with a large central lumen for the aspiration of thrombus. It may be necessary to remove the catheter to clear thrombus; the RX system provides guidewire access through this process. The aspiration lumen should be as large as possible to accommodate the thrombus.

The obstruction (e.g., thrombus) is removed by advancing the catheter along the lumen and rotating the catheter in the direction of the spiral. In another embodiment, the spiral tip may be advanced directly toward the obstruction without rotation to remove it.

The guidewire lumen may be connected to a suction source for removal of the thrombus after it has been detached from the blood vessel. The angled tip of the catheter provides for the effective retrieval of the thrombus.

A method of forming a catheter for removing an obstruction from a blood vessel is also disclosed. First, an elongate flexible catheter body comprising a proximal end, a distal end, and at least one lumen having a guidewire extending therethrough is extruded. Next, the catheter tip is formed having a cutting edge spirally tapered along a length of the catheter. The catheter tip is then attached to the distal end of the elongate flexible catheter body. In some embodiments, the catheter tip is formed from a mold. In other embodiments, the catheter tip is formed by cutting a length of catheter tubing in a spiral pattern.

BRIEF DESCRIPTION OF THE DRAWINGS

A detailed description of various aspects, features, and embodiments of the subject matter described herein is provided with reference to the accompanying drawings, which are briefly described below. The drawings are illustrative and are not necessarily drawn to scale, with some components and features being exaggerated for clarity. The drawings illustrate various aspects and features of the present subject matter and may illustrate one or more embodiment(s) or example(s) of the present subject matter in whole or in part.

DETAILED DESCRIPTION OF EXEMPLARY EMBODIMENTS

Figure 1:
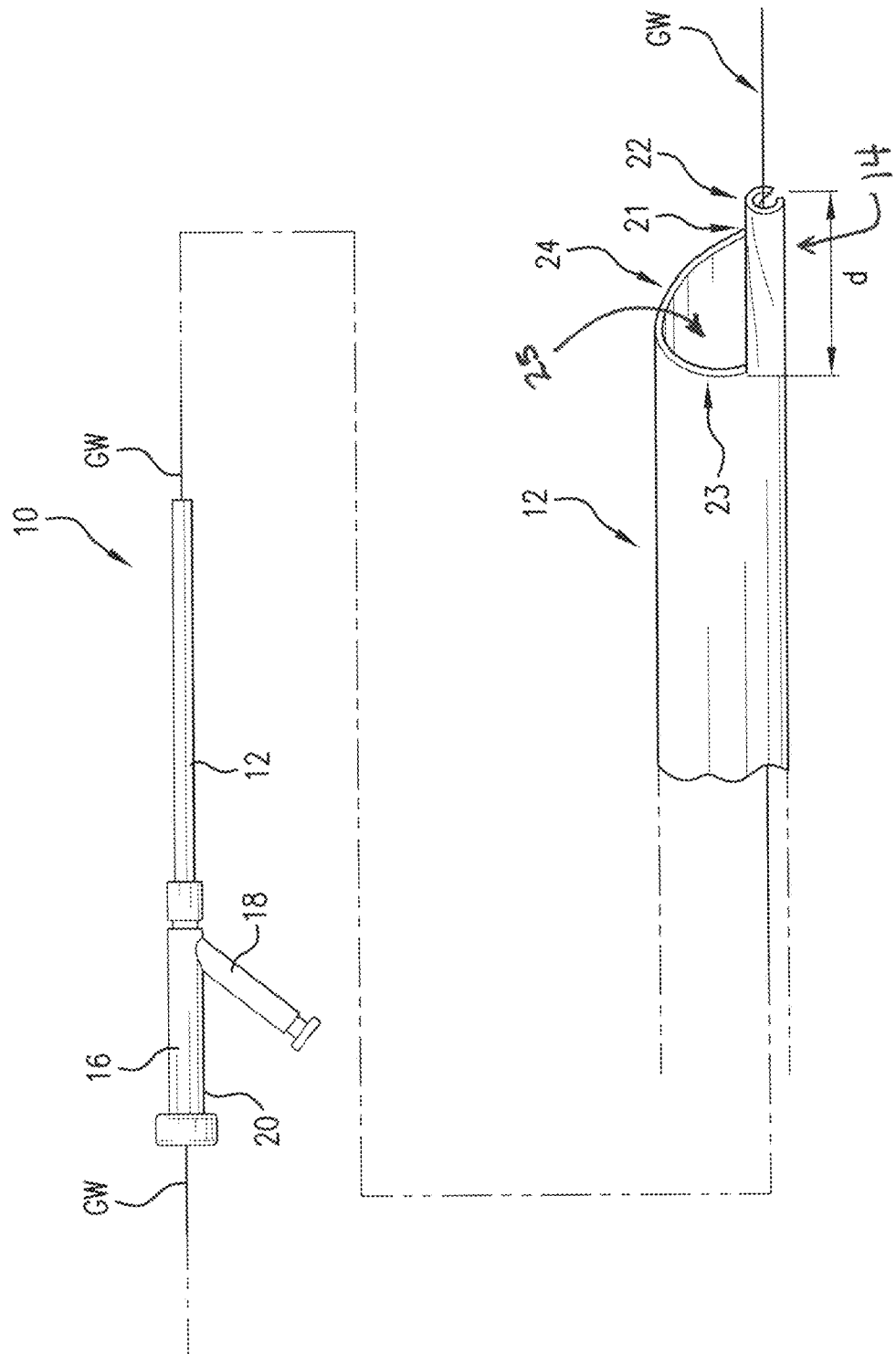
FIG. 1 is a side elevational view of the catheter shown introduced over a guidewire.

A catheter for removing an obstruction from a blood vessel is provided as illustrated in FIGS. 1 to 4. Referring now to FIG. 1, The catheter 10 includes an elongate tubular body 12 having an inner wall and an outer wall, a distal end, an opposing proximal end, and a tip 14. An aspiration lumen 25 is defined by the inner wall of the elongate tubular body 12. And the tip defines an aspiration port. The tip 14 includes a leading edge 24 and a trailing edge 23 which defines an asymmetrical helical or spiral tip portion. The helical tip portion defined by the leading 24 and trailing edges 23 of the elongate tubular body walls can be used to manipulate an obstruction from the vessel wall during aspiration to facilitate removal of the obstruction from the vasculature. The catheter 10 can be a rapid exchange catheter or an over-the-wire catheter. Preferably, the catheter is about 145 cm in length.

The catheter 10 includes a proximal hub 16 at the proximal end of the elongate tubular body 12. The hub includes or is in communication with a source of negative pressure to aspirate via the aspiration port and aspiration lumen and remove occlusions in the blood vessels. The source of negative pressure 18 can be a vacuum, syringe, mechanical pump or bulb or any other suitable source of negative pressure known by those of ordinary skill in the art. Other aspiration methods such as those using a venturi effect can be employed.

The elongate body 12 can be formed of a variety of materials, including metal, plastic and composite materials. In one embodiment, proximal portion of elongate tubular body 12 is manufactured as a metal tube, for example, as a stainless steel hypotube, and may be coated with a polymeric material such as PTFE. The metal tube may also be covered with a single or multilayered plastic material through one or more processes, including coextrusion, dipping, heat-shrinking, and electrostatic and thermal coating.

In another embodiment, elongate body 12 is manufactured as a plastic tube. Materials suitable for use in the catheter tube include, but are not limited to, Polyurethanes (PU), such as Tecoflex, Pellethene, Bionate, corethane, Elasteon, and blends thereof; Polyethylenes (PE), such as PET, PBT, PVDF, Teflon, ETFE, and blends thereof, Polyolefins, such as HDPE, PE, LDPE, LLDPE, Polypropylene, and blends thereof, Polyimides; Polyamides; all classes of Nylons, such as Nylon 11, Nylon 12, Nylon 6, 6, Nylon 6, Nylon 7, 11, Nylon 11, 12, and blends thereof); block copolymers; PEBA-types polymers, such as ELY, PEBAX, Ubesta, and blends thereof, and biodegradable polymers.

Suitable materials for the elongate tubular body 12 also include blends of the above mentioned materials as well as any composite materials, like dual-layers, tri-layers and multi-layers thereof. For example, catheter body may be produced from a tube comprising an outer layer made of Nylon and an inner layer made of a lubricious material such as polyethylene or PTFE. A metallic or nonmetallic braiding may also be included within or between layers of the body. For example, in one embodiment, a fluoropolymer lined, braided catheter tubular body can be used. For the purpose of illustration, the fluoropolymer liner can have a thickness of about 0.03 mm, the outer polymer layer can have a thickness of about 0.05 mm, and the braid reinforcement can have a thickness of about 0.03 to about 0.06 mm. Preferably, the wall minimum thickness of the elongate tubular body is about 0.11 or 0.14 mm. The tubular body can have sections of varying durometer and/or materials along the length of the body to achieve a varying stiffness. It is further contemplated that catheter 10 can be constructed of any biocompatible material. As such, catheter 10 can be constructed from the above-identified polymers, combinations or blends of these polymers, whether alone or in combination with other materials, or other bioabsorbable materials.

Elongate tubular body 12 can be manufactured using a variety of known techniques such as but not limited to: extrusion, injection molding, air-blowing, stretching, deep drawing, polymerization, cross-linking, dipping from solution, powder depositioning, sintering, electro-spinning, melt spinning, deformation under temperature, stretch blowing, chemical grafting any combination of the above with reinforcement element like metal braids, coils, glass fibers, carbon fibers and other kind of organic or inorganic fibers, liquid crystals, as well as classical machining technologies like milling, drilling, grinding, etc. In the event that metallic elements such as hypotubes, are to be incorporated, various metallic manufacturing techniques can be used, such as but not limited to, machining, tube drawing processes, drilling, milling EDM, other deformation methods, plating sputtering, electrografting, sintering, and depositioning e-polishing, among others.

Additionally, elongate tubular body 12 can be constructed from polypropylene or urethane by an extrusion process using an extruder such as that available any of a number of known suppliers, such as Medical Extrusion Technologies, Inc. Murieta, Calif. U.S. Biosynthetic polymer materials can be constructed in a bioreactor according to the process disclosed in U.S. Pat. No. 6,495,152, the entirety of which is hereby incorporated by reference. The materials can be post processed in a number of ways including, for example and not by way of limitation, extrusion, molding, such as by injection or dipping, textile processing such as weaving or braiding, and forming. Forming processes that can be suitable are rolling and welding sheets of material or vacuum forming into tubular shapes, to name only a few examples.

The tubular body 12 can be further coated with any of a variety of materials and techniques to enhance performance if desired, including a number suitable coatings and coating techniques subject to patent matters owned by Abbott Laboratories such as U.S. Pat. Nos. 6,541,116, 6,287,285, and U.S. Patent Publication No. 2002/0009535, the entireties of which are hereby incorporated by reference. For example, possible coating materials include lubricious materials such as Teflon® available from DuPont De Nemours, Wilmington, Del., U.S., and hydrophobic materials such as silicone lubricant dispersion PN 4097, available from Applied Silicone Corp., Ventura, Calif., U.S., or hydrophilic materials such as hydrogel available from Hydromer, Branchburg, N.J., U.S., or lubricious coatings such as those available from Hydro-Silk of Merritt Island, Fla., U.S.

The elongate tubular body 12 includes tip 14 is defined by leading edge 24 and trailing edge 23 to form an asymmetrical helical or spiral taper along the length of the tip portion.

Figure 4:
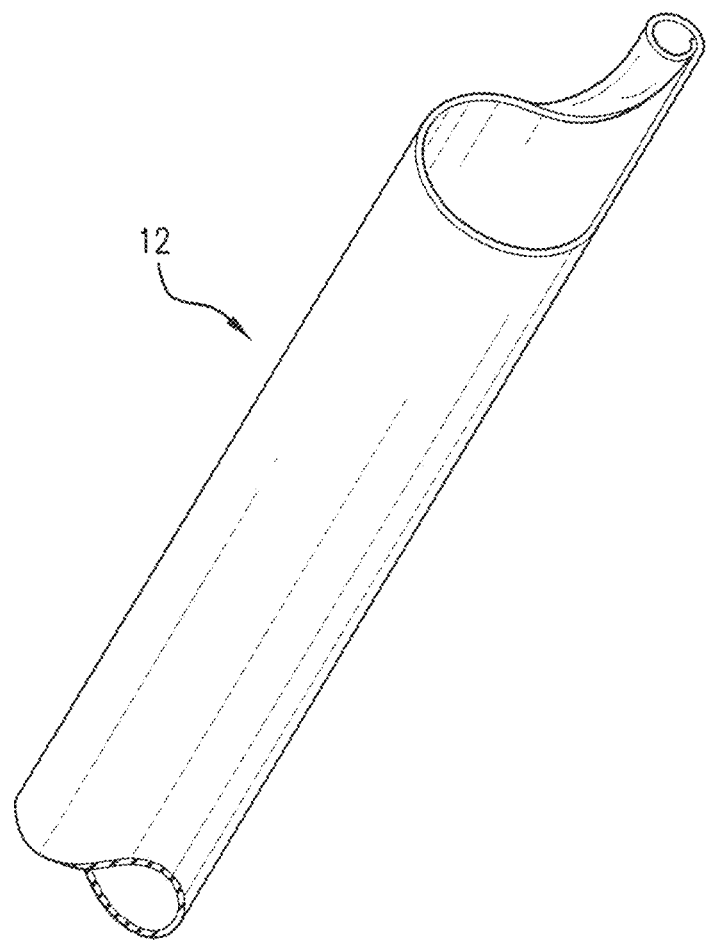
FIG. 4 is a perspective view of tip of the catheter of FIG. 1.

The asymmetrical helical or spiral taper defines an oblique angle relative to the longitudinal axis of the elongate tubular body 12. The helical configuration provides a non-traumatic cutting edge to the distal end of catheter 10 to facilitate removal of occlusions within the blood vessel. The cutting edge of the spiral catheter is preferably sinusoidal and/or curved as depicted in FIG. 1 and FIG. 4.

The oblique angle defined by the tip is approximately 10 degrees to 80 degrees relative to the longitudinal axis of the elongate tubular body 12, depending on the size of the catheter diameter. For example, a catheter having a diameter of 3 French preferably has a minimum tip angle of 45 degrees, and a maximum tip angle of about 80 degrees. A catheter having a diameter of 9 French preferably has a minimum tip angle of about 35 degrees and a maximum tip angle of 70 degrees. "Tip angle" as used herein refers to the angle at the beginning of the helical tip at the distal end of the catheter. The tip angle defined by the helical or spiral configuration is configured to lift thrombus and other debris from the vascular wall by advancing and rotating the catheter. The configuration provides a greater cross-sectional area providing greater force than a catheter tip with a diagonal cut.

Figure 2A:
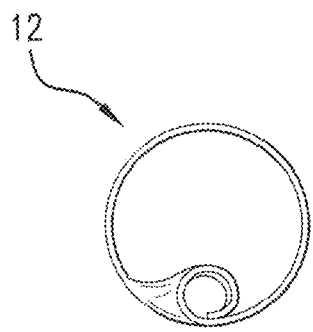
FIGS. 2A-2D are views of the tip of the catheter showing various angles of the tip.
Figure 2B:
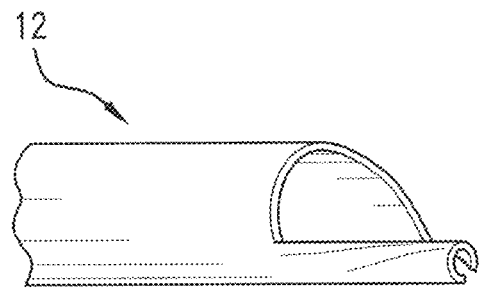
Figure 2C:
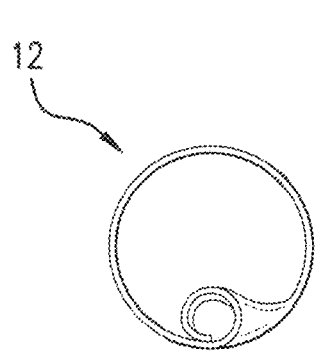
Figure 2D:
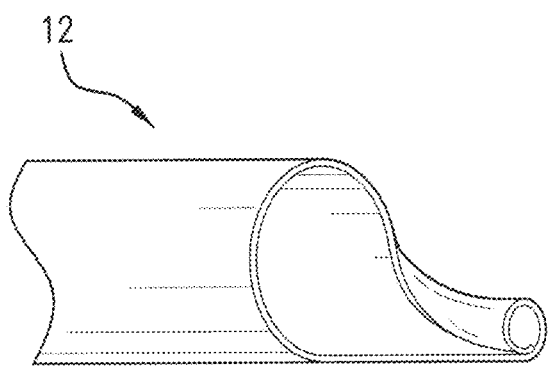
Figure 3:
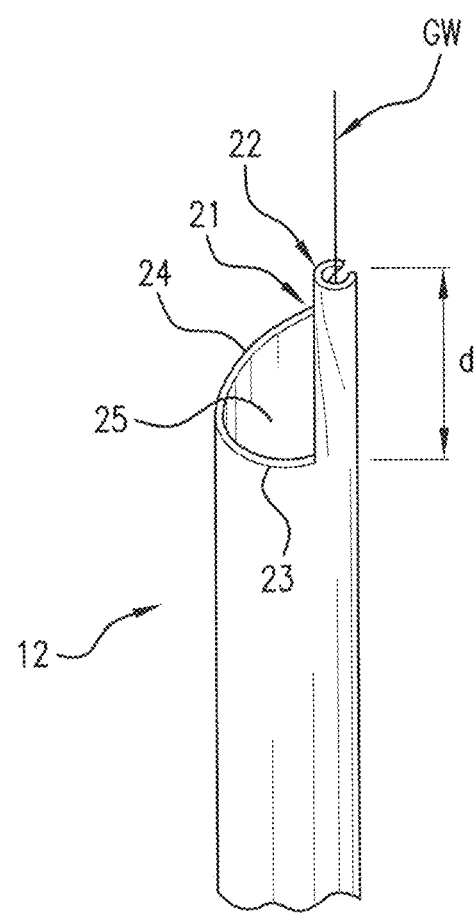
FIG. 3 is a side view of the tip of the catheter of FIG. 1.

The spiral or helix of the tip can have a clockwise direction, as illustrated in FIGS. 2A-2B. Alternatively, the tip can have a counterclockwise direction, as illustrated in FIGS. 2C-2D. The direction of the spiral may be dictated by the age of the obstruction, the direction of curvature of the artery in which the catheter is placed, or the handedness of the inverventionalist using the catheter. Thus, the cutting edge of the spiral catheter can be shaped to accommodate a clockwise or a counterclockwise rotation.

In some embodiments, the tip 14 comprises a radiopaque material, such as platinum or gold. Alternatively, a material such as BaS04 may be incorporated into tip 14 when it is formed. The radiopaque material allows an interventionalist to properly position the catheter 10 within a patient's body.

The length of the spiral or helical tip is approximately 5 mm to 20 mm. For example, with a 3 French catheter, the angle of the spiral tip may be approximately 10 degrees and the length of the tapered tip may be approximately 0.2 mm or, with an 8F catheter, the angle of the spiral tip may be approximately 80 degrees and the length of the spiral tip may be approximately 50 mm.

Catheter tip 14 can be configured to provide atraumatic contact between elongate body 12 and a wall against which elongate body 12 may be pushed during a treating procedure. The tip can be designed to have any length (d) extending from the catheter body 12 distal end. For example but not limitation, length d can be about 2.5 mm to about 25 mm. The catheter tip can be configured as a soft tip, which in some embodiments, can be composed of a soft sleeve that is affixed on and that extends beyond distal end of the aspiration lumen, or, alternatively, that is affixed on and extends beyond the lumen of elongate body 12. Typically, a soft tip is affixed through a welding process, but other affixing techniques are also included within the scope of the present invention, for example, adhesive bonding. Suitable materials for the tip can be chosen from any material suitable for producing elongate body 12. The tip may be manufactured from a material softer than elongate body 12, or from any of the materials or combinations of materials described with reference to elongate body 12. In one embodiment, the tip is manufactured from a material having the same basic composition as, but a lower Shore durometer hardness than the elongate tube 12 material. In another embodiment, the tip may be manufactured from a blend of PEBAX 55D and PEBAX 63D polymers. One skilled in the art will recognize that the tip 14 may be manufactured from a variety of other materials according to the previous description of materials, for example, a polyurethane, a polyethylene, a polyolefin, a polyimide, a polyamide like Nylon, a block copolymer, or blends, or compositions or dual layers or multi-layers thereof.

Referring to FIG. 1, guidewire GW is disposed within guidewire lumen 22. Guidewire lumen 22 is alongside of aspiration lumen 25. Guidewire lumen can be disposed exterior to the elongate tubular body (not shown), or alternatively, within elongate tubular body 12, as depicted in FIGS. 2A and 2C. Guidewire lumen can extend from hub 16 to distal end region of elongate tubular body 21. The guidewire lumen can be located only on the distal end of the elongate tubular body of catheter or extend the entire length of the elongate tubular body if desired. Accordingly, the guidewire lumen can have a distal end that is distal to the aspiration port and elongate catheter shaft distal end 21. For example, in one embodiment, the guidewire lumen extends less than 40 cm proximally from the distal end of the tubular body. In another embodiment, the guide wire lumen is closer to the distal end of the elongate tubular body than it is to the proximal end of the tubular body. In any arrangement, the aspiration lumen is unobstructed by the guidewire lumen. Guidewire is formed from a metallic material or a rigid polymeric material.

Elongate tubular body 12 can further include one or more side apertures disposed throughout the inner and outer walls of the body. In one embodiment, the side aperture(s) is located in a distal portion of the elongate tubular body 12. Side apertures (not shown) can facilitate thrombus removal about 6 or less hours post symptom onset.

The aspiration port may be fitted with a valve (not shown) which allows an interventionalist to control the rate and level of aspiration. For example, the valve can quickly be opened and closed to provide short bursts of aspiration.

The aspiration lumen 25 may be connected to a suction source via vacuum port 18 for removal of the thrombus after it has been detached from the blood vessel. Alternatively, a capture device (not shown) may be deployed beyond the distal tip 14 to catch any debris that is dislodged during the removal of the obstruction. An exemplary embodiment of a capture device is described in U.S. Pat. No. 7,316,702, which is hereby incorporated by reference in its entirety. In another embodiment, the capture device may be an inflatable member (not shown) that can be inflated to block the passage of any debris that is dislodged during the thrombectomy. The inflatable member is preferably a compliant balloon formed of an elastic material such as latex.

One exemplary method in accordance with use of the aspiration catheter described herein is removal of plaque and any associated occlusion, such as for example, thrombi from a blood vessel. Generally, a guide catheter is introduced into the patient's vasculature through the patient's femoral artery. The guide catheter typically has a large lumen sized to fit and guide the introduction of the aspiration catheter. The guide catheter is advanced to the ostium of the blood vessel. A guide wire is then advanced into the thrombosed artery and through the thrombus. An embolic protection catheter with an occlusive balloon or net structure is then advanced over the guide wire and through the thrombus and positioned distal to the thrombus where it is deployed and expanded. Thereafter, the aspiration catheter 10 may then be advanced over the guide wire so that the distal tip 14 of the aspiration catheter is positioned at or near the target thrombus. The intereventionalist can position the aspiration catheter proximally increasing the distance between the tip of the aspiration catheter and the balloon from the occlusion device. Aspiration can occur proximal to the occlusion device. Removal of an obstruction (e.g., thrombus) and debris can be facilitated by rotating the helical or spiral leading edge 24 in the direction of the target thrombus until it has been detached from the vessel wall. In another embodiment, the leading edge 24 may be advanced directly toward the obstruction without rotation. The debris and obstruction can be removed by suction or aspiration from the blood vessel. Additionally, once aspiration occurs, additional blood flow will flow at the site to create shear stresses which will further facilitate removal of the debris from the vessel wall.

It is understood that the subject matter described herein is not limited to particular embodiments described, as such may, of course, vary. It is also understood that the terminology used herein is for the purpose of describing particular embodiments only, and is not intended to be limiting, since the scope of the present subject matter is limited only by the appended claims. Where a range of values is provided, it is understood that each intervening value between the upper and lower limit of that range and any other stated or intervening value in that stated range, is encompassed within the disclosed subject matter. While the subject matter has been described and pointed out in detail with reference to exemplary embodiments, it will be understood by those skilled in the art that various changes, modifications, substitutions, and omissions can be made without departing from the spirit of the disclosed embodiments. It is therefore intended that the claimed invention embrace those equivalents within the scope of the claims that follow.

What is claimed is:

1. A catheter for removing an obstruction from a blood vessel comprising:
   an elongate tubular body comprising a proximal end and a distal end, wherein an aspiration lumen and a guidewire lumen extend through the elongate tubular body, the aspiration lumen and the guidewire lumen each having a central longitudinal axis, the aspiration lumen and the guidewire lumen aligned such that the central longitudinal axis of the guidewire lumen extends into the aspiration lumen with the central longitudinal axis of the guidewire lumen radially offset from the central longitudinal axis of the aspiration lumen, wherein the distal end of the elongate tubular body includes a leading edge and a trailing edge defining an asymmetrical taper and a cutting edge, the cutting edge configured to manipulate an obstruction from a vessel wall during aspiration; and
   a tip radially offset from the central longitudinal axis of the aspiration lumen, the tip including at least a portion of a leading edge of the guidewire lumen, and wherein the leading edge of the guidewire lumen is distal to a leading edge of the aspiration lumen.

2. The catheter according to claim 1, wherein a portion of the tip is about 5 mm to 20 mm in length.

3. The catheter according to claim 1, wherein an external diameter of the elongate tubular body is about 3 French to 8 French.

4. The catheter according to claim 1, wherein the tip includes a wall integral with the distal end of the elongate tubular body, the wall including a helical taper having a clockwise direction.

5. The catheter according to claim 1, wherein the tip includes a wall integral with the distal end of the elongate tubular body, the wall including a helical taper having a counterclockwise direction.

6. The catheter according to claim 5, wherein the helical taper defines a sinusoidal or curved configuration.

7. The catheter of claim 1, wherein the aspiration lumen includes an aspiration port, and wherein the aspiration lumen is defined by at least a portion of a wall of the elongate tubular body.

8. The catheter of claim 7, wherein the aspiration port is defined by at least a portion of the tip.

9. The catheter of claim 8, wherein the guidewire lumen extends from the elongate tubular body to through the tip.

10. The catheter of claim 9, wherein the guidewire lumen is disposed exterior to the elongate tubular body.

11. The catheter of claim 9, wherein the guidewire lumen extends from an inner wall of the elongate tubular body.

12. The catheter of claim 9, wherein the guidewire lumen extends less than 40 cm proximally from the distal end of the elongate tubular body.

13. The catheter of claim 12, wherein a proximal end of the guidewire lumen is closer to the distal end of the elongate tubular body than to the proximal end of the elongate tubular body.

14. The catheter of claim 1, wherein the tip is formed from a material that has a lower durometer than a material of the elongate tubular body.

15. The catheter of claim 1, wherein the elongate tubular body includes a side aperture extending through inner and outer walls of the elongate tubular body.

16. The catheter of claim 1, wherein the elongate tubular body comprises an inner polymeric layer, an outer polymeric layer, and a support layer therebetween.

17. The catheter of claim 16, wherein a lubricious coating is disposed on a surface of the inner layer.

18. The catheter of claim 16, wherein the support layer includes braided material.

19. The catheter of claim 1, wherein the catheter is a rapid exchange catheter.

20. The catheter of claim 1, wherein the catheter is an over-the-wire catheter.

* * * * *